US007842023B2

(12) United States Patent
Chinol et al.

(10) Patent No.: US 7,842,023 B2
(45) Date of Patent: Nov. 30, 2010

(54) CONTAINER FOR VIAL OF RADIOPHARMACEUTICAL AND SET FOR ITS INFUSION IN A PATIENT OR FOR ITS TRANSFER ELSEWHERE

(75) Inventors: Marco Chinol, Rome (IT); Giovanni Paganelli, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 1388 days.

(21) Appl. No.: 10/503,976

(22) PCT Filed: Feb. 3, 2003

(86) PCT No.: PCT/IT03/00049

§ 371 (c)(1), (2), (4) Date: Aug. 10, 2004

(87) PCT Pub. No.: WO03/069632

PCT Pub. Date: Aug. 21, 2003

(65) Prior Publication Data

US 2005/0154275 A1 Jul. 14, 2005

(30) Foreign Application Priority Data

Feb. 11, 2002 (IT) ......................... RM2002A0071

(51) Int. Cl.
*A61B 19/00* (2006.01)
*G21F 5/00* (2006.01)

(52) U.S. Cl. .................. 604/403; 250/506.1; 250/507.1

(58) Field of Classification Search .............. 250/506.1, 250/507.1; 604/403, 407, 411
See application file for complete search history.

(56) References Cited

U.S. PATENT DOCUMENTS 3,673,411 A * 6/1972 Glasser .................... 250/506.1
3,769,490 A 10/1973 Czaplinski
4,233,973 A 11/1980 Shukla
4,745,907 A 5/1988 Russel, Jr. et al.
4,851,702 A * 7/1989 Perlman .................. 250/507.1
5,397,902 A * 3/1995 Castner et al. ........ 250/432 PD
5,810,768 A * 9/1998 Lopez ........................ 604/500
5,944,190 A * 8/1999 Edelen .................... 206/524.4
6,113,555 A * 9/2000 Parmigiani .................. 600/579
6,344,031 B1 * 2/2002 Novacek et al. ............. 604/195
6,366,633 B1 * 4/2002 Stezaly et al. ............... 376/202

FOREIGN PATENT DOCUMENTS

GB 1136194 A * 11/1968
GB 1136194 12/1974

OTHER PUBLICATIONS

Office Action issued for corresponding Australian Application No. 2003209692, mailed Apr. 26, 2007 (6 pages).

* cited by examiner

*Primary Examiner*—Melanie J Hand
(74) *Attorney, Agent, or Firm*—Lucas & Mercanti, LLP

(57) ABSTRACT

A container for a vial of radiopharmaceutical, made of polymethyl methacrylate consists of a receptacle, with a cavity capable of containing the vial of radiopharmaceutical, and of a lid screwed onto the receptacle for closing the container, said lid presenting a central through-hole. A set, in combination with this container with the vial of radiopharmaceutical, consisting of a bottle of saline solution and two infusion catheters, enhances the radioprotection during the infusion of a radiopharmaceutical in an infusion operation.

29 Claims, 3 Drawing Sheets

Figure 2:
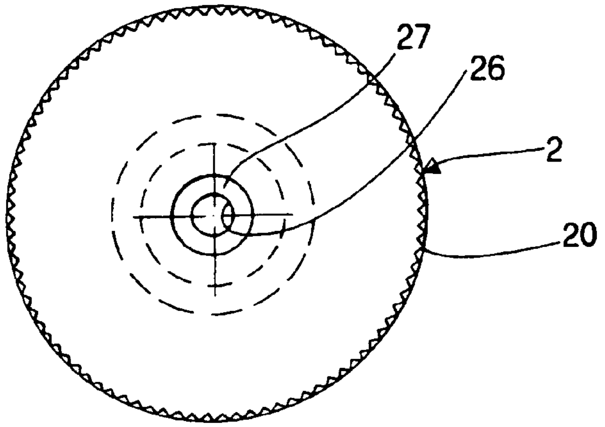

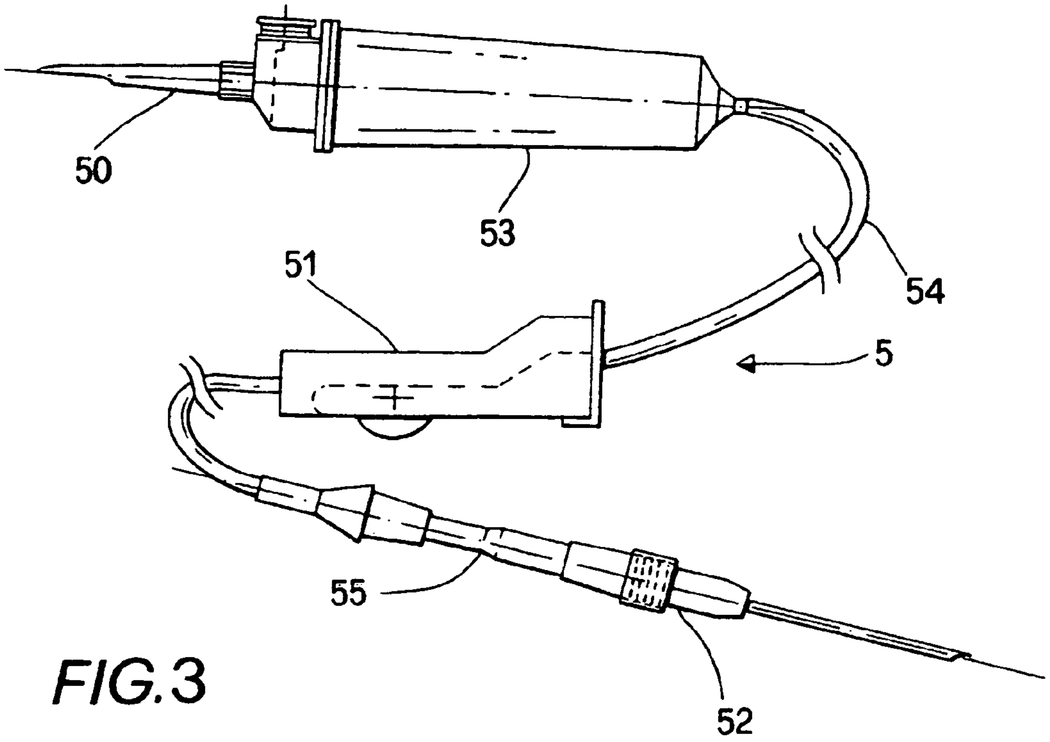
FIG. 3
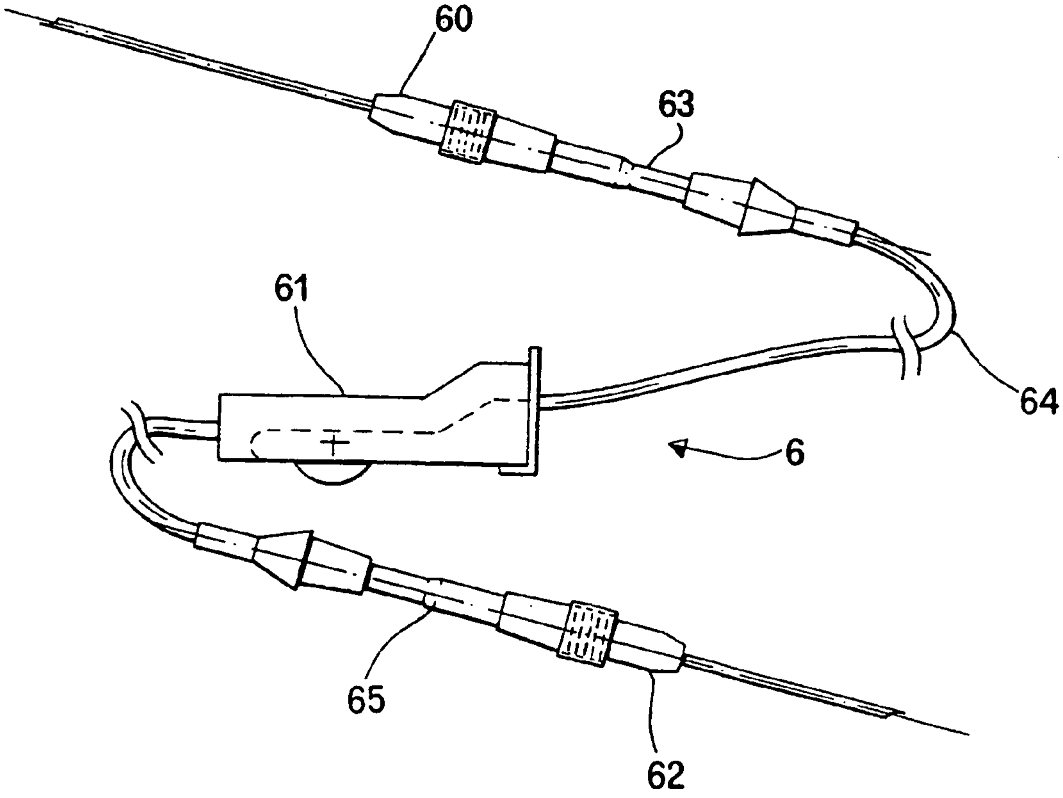

CONTAINER FOR VIAL OF RADIOPHARMACEUTICAL AND SET FOR ITS INFUSION IN A PATIENT OR FOR ITS TRANSFER ELSEWHERE

This application is the US national phase of international application PCT/IT03/00049 filed 03 Feb. 2003, which designated the U.S. and claims priority to IT Application No. RM02A000071 filed 11 Feb. 2002. The entire contents of these applications are incorporated herein by reference.

The invention described herein relates to a container for a vial of radiopharmaceutical as well as a set for the infusion of the radiopharmaceutical from the vial housed in the container into a patient or for the transfer of the radiopharmaceutical elsewhere.

Currently, radiopharmaceuticals, and particularly but not exclusively, those containing beta-emitting radioisotopes generally destined for infusion into patients, are contained in vials for intravenous injection, equipped with a hermetically sealed rubber cap through which the needle of a syringe is inserted for the extraction of the radiopharmaceutical to be injected or for its transfer elsewhere to a different receptacle, Traditionally, the radiopharmaceutical vials are in turn housed in a lead container.

This type of radioprotection using lead containers presents many drawbacks both from the point of view of storage and transportation of the radiopharmaceutical and from that of its subsequent handling for use. Lead containers are heavy, a factor which has a substantial adverse effect on the transportation and storage of the radiopharmaceutical. What is more, owing to their opacity, lead containers prevent visualisation of the contents of the radiopharmaceutical vial. The operator, in fact, has to open them to check their contents and state of conservation, check for any breakage of the vial with a major risk of contamination, and, if required, check the dose of radioactivity.

Moreover, in the administration of a radiopharmaceutical to a patient or when transferring it to another receptacle. The operator handling it or aspirating it with a syringe or some other device risks receiving a dose of radiation even as a result of contact with the radiopharmaceutical itself.

Another by no means negligible problem in intravenous infusion is that of accurately measuring the amount of radioactive substance infused. This problem was addressed, for example, in U.S. Pat. No. 5,529,189 granted to Feldschuh on Jan. 25, 1996. The aim of that patent was to provide a disposable set for administering a precise dose of radioactive substance to a subject with an accuracy of at least 99.9% by weight. Nevertheless, even if this objective is effectively achieved, the fact remains that according to the above-cited patent the vial of radioactive substance has to be handled with great care owing to the substantial risk to the operator.

One of the objectives of the invention described herein is therefore to provide a container for vials of radiopharmaceutical made of a material capable of shielding the operator from radioactive emissions, and particularly beta-emitting isotopes.

Another objective of the present invention is to provide an easily manageable, light-weight container.

Yet another objective of the present invention is to provide a container for vial of radiopharmaceutical that enables the contents to be identified without needing to open it.

Another objective of the present invention is to allow the shipment and transportation of precalibrated, customised radiopharmaceuticals for individual patients in containers in which the radiopharmaceutical can be checked by the operator as corresponding to the dosage amount desired.

Yet another objective of the present invention is to allow the infusion of the radiopharmaceutical in a patient or its transfer elsewhere without any need for handling the vial of radiopharmaceutical.

One initial aspect of the present invention aims at achieving the above-mentioned objectives by providing a container for vial of radiopharmaceutical made from a material suitable for shielding the operator from the radiation emitted by the radiopharmaceutical through the vial and consisting of a receptacle with a cavity capable of containing the vial of radiopharmaceutical and of a lid coupled to the receptacle for closing the container, said lid being equipped with a central through-hole.

One initial additional objective of the present invention is to allow infusion of the radiopharmaceutical in a patient or its transfer elsewhere without any need to aspirate the radiopharmaceutical with syringes in order to extract it from the vial.

A second additional objective of the present invention is to allow accurate measurement of the amount of radiopharmaceutical infused in a patient or transferred elsewhere to a different receptacle by reading its volume.

A second aspect of the present invention aims at achieving the above-mentioned additional objectives by providing a set in combination with the above-mentioned container housing the radiopharmaceutical vial and consisting of:

- a saline solution bottle containing saline solution;
- an infusion catheter equipped with twin connectors, one for inserting a needle into the bottle of saline solution and a second connector for a second needle, inserted, via the central through-hole in the lid, into the cap of the vial of radiopharmaceutical in such a way as not to be immersed in the radiopharmaceutical;
- a second infusion catheter equipped with twin connectors, one for the insertion of one needle, via the through-hole in the lid, into the cap of the vial of radiopharmaceutical, and the other for a second needle inserted in the patient's vein or elsewhere, the first needle of this second catheter being long enough to touch the bottom of the vial of radiopharmaceutical.

Figure 1:
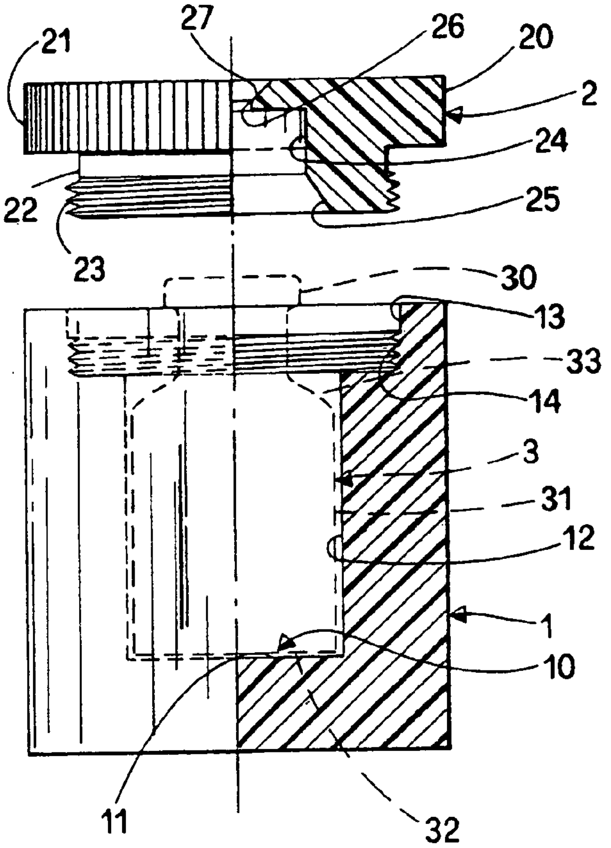
Figure 5:
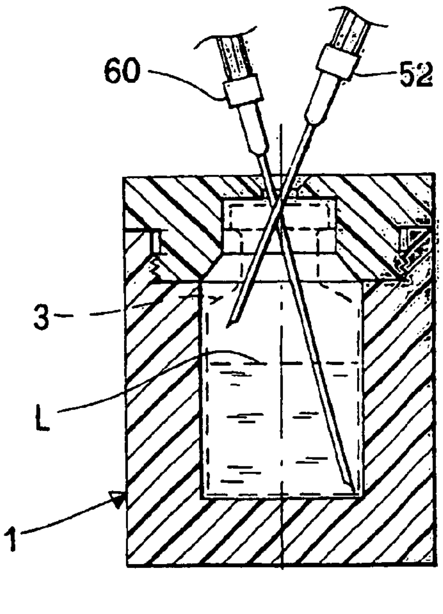
Figure 4:
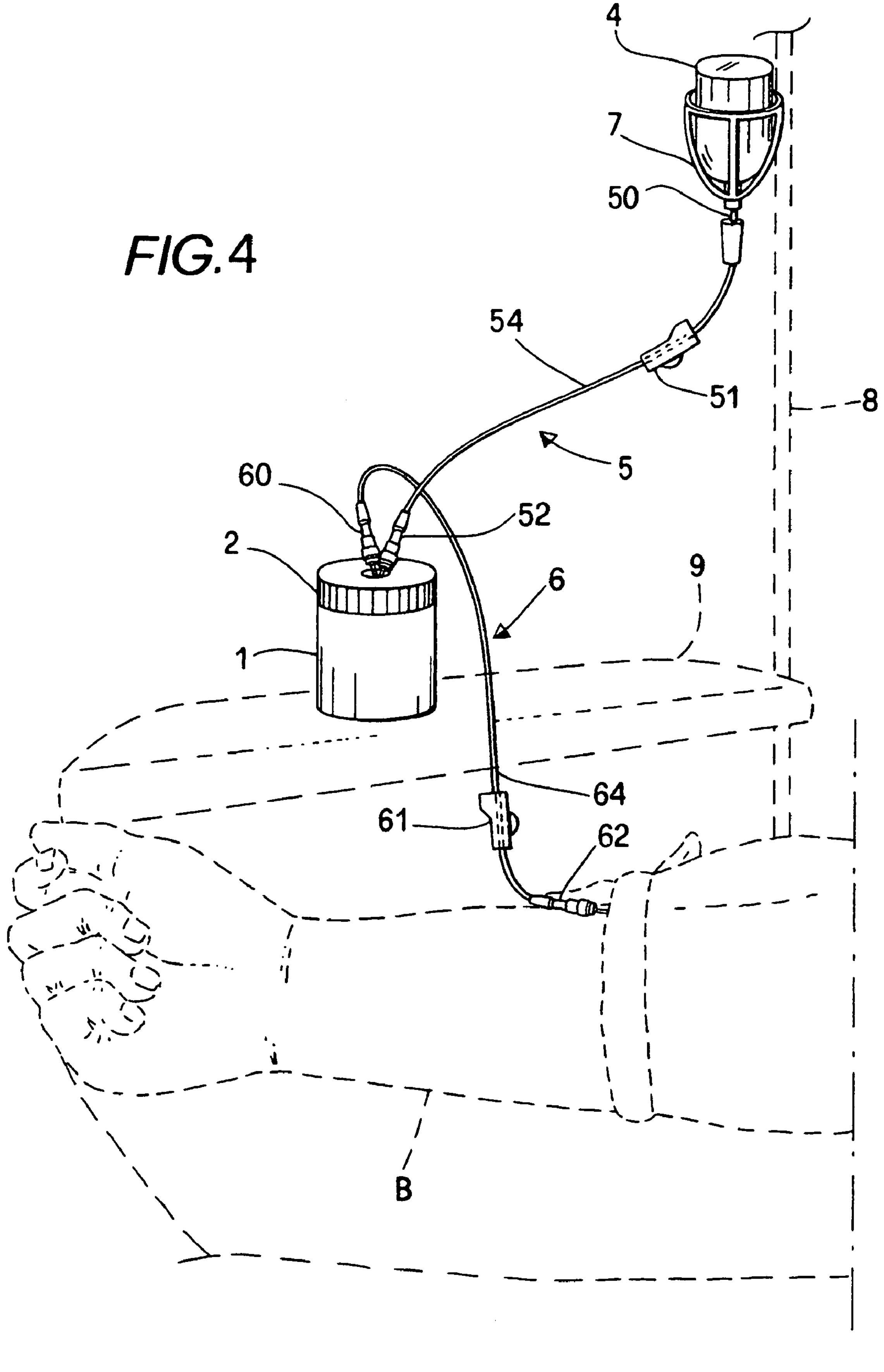

The invention described herein will now be described with reference to a preferred execution form, though it is understood that executive variants may be implemented without, however, departing from the framework of protection of the present invention and referring to the figures in the attached drawings, in which:

FIG. 1 presents a side view in the left-hand half and an axial longitudinal section of the receptacle and its separate lid in the right-hand half, illustrating both the components of a radiopharmaceutical vial container according to the present invention;

FIG. 2 presents a plan view from above of the container as in FIG. 1;

FIG. 3 presents a schematic plan view of part of the set for the use of the radiopharmaceutical vial container as in FIGS. 1 and 2 in extracting the radiopharmaceutical;

FIG. 4 presents a schematic perspective view of the container and the set according to the present invention in an infusion operation;

FIG. 5 presents an enlarged-scale longitudinal section of the container as in FIG. 1 with the needles inserted.

With reference to the drawings, FIGS. 1 and 2 show the radiopharmaceutical vial container according to the invention, partly in section, partly in side view, and from above, respectively. It consists of receptacle 1 and lid 2. A radiopharmaceutical vial for intravenous infusion is represented in FIG. 1 with dashed lines and is marked 3. The radiopharmaceutical vial 3 is traditionally a cylindrical UNI 6255 pressed glass vial, or other similar receptacle conventionally used for the same purpose, with an externally enlarged wide mouth 30 on which a rubber cap (not shown) is hermetically sealed with an aluminium crimp-cap seal. Vial 3, e.g. a 20 ml vial, has a cylindrical wall 31, a bottom 32 and a portion 33 widening downwards from mouth 30 to cylindrical wall 31. The radiopharmaceutical to be contained in the vial is a beta-emitting isotope, such as $^{90}$Y-biotin, $^{90}$Y-DOTATOC, $^{90}$Y-MoAbs amongst others.

Receptacle 1 is preferably cylindrical and has a cavity 10, which is also cylindrical, capable of containing radiopharmaceutical vial 3 with a mobile coupling. That is to say, it is preferable that the diameter of cavity 10 should be slightly larger than the outside diameter of wall 31 of cylindrical vial 3 so that the latter, which rests on the bottom 11, is prevented from making excessive radial movements and consequently knocking against vertical wall 12 of receptacle 1.

In its upper part cavity 10 widens into compartment 13 of greater diameter whose inner wall presents a threaded portion 14. As can be seen in FIG. 1, the height of cavity 10 is such that the vial projects with its mouth 30 beyond the upper rim of vertical wall 12 of receptacle 1.

Lid 2 is screwed onto receptacle 1 to close the container. Lid 2 is likewise cylindrical and advantageously is formed in one piece from an upper disk 20 of the same diameter as receptacle 1. The upper disk 20, the rim of which presents a milled or knurled edge 21, to enhance the tightness of fit of lid 2, extends downwards in a similar cylindrical portion 22, with a diameter measuring less than that of the upper disk. The size of cylindrical portion 22 is such that it fits into compartment 13 of receptacle 1 of smaller diameter. Cylindrical portion 22 presents an outside counterthread 23 to create a threaded coupling with the inside thread 14 of the receptacle. Clearly, the closure of lid 2 on receptacle 1 of the container can also be of different design, e.g. with a bayonet coupling.

When lid 2 is fully screwed onto receptacle 1, the vial of radiopharmaceutical is held in place between the bottom 11 of receptacle 1 and the underside of lid 2 so that it cannot move. To this end, as illustrated in FIG. 1, lid 2 is hollow on the inside. It presents a cyclindrical upper compartment 24 with a diameter slightly larger than that of vial mouth 30, flaring downwards into a hollow truncated-cone portion 25 that follows the profile of portion 33 of the vial between mouth 30 and cylindrical wall 31.

Moreover, as is better illustrated in FIG. 2, lid 2 presents, above its cylindrical upper compartment 24, a central through-hole 26 with a diameter close to that of the central portion of the rubber cap of radiopharmaceutical vial 3 which is accessible for the insertion of an aspiration needle. To facilitate this operation, central through-hole 26 has an outward-facing upper flared portion 27.

According to the invention described herein, at least receptacle 1, but preferably also lid 2, is made of transparent material. In this way, an operator can check the contents of the vial of radiopharmaceutical and its volume without having to remove lid 2 and lift up the vial. The dose can therefore be calculated on the basis of the concentration (activity/volume) declared by the manufacturer, thereby avoiding the operator having to expose himself to ionising radiation.

If the radiation emitted by the radiopharmaceutical is beta-radiation, the material receptacle 1 is made of is polymethyl methacrylate, known under the trade name of plexiglas.

Lid 2 can also be made of the same material.

Polymethyl methacrylate has excellent shielding characteristics against radioactive emissions, and particularly against beta-emitting isotopes.

In addition, polymethyl methacrylate has a low volumic mass and is thus capable of providing a light-weight, easily manageable container.

The container has a thickness, both of the wall of the receptacle and that of the lid, that will depend on the beta-emission energy of the isotope it contains. This thickness will be determined by the expert in the sector, simply on the basis of his general knowledge of the subject.

In a different realisation of the invention, the radio-pharmaceutical can also consist of mixed emitters, i.e. isotopes that emit both beta and gamma radiation (including 511 KeV annihilation photons), and also those with mixed emission such as, for example, $^{131}$I, and il $^{177}$Lu.

In the particular case of [$^{18}$F]FDG, in view of its extensive use in clinical practice, the device is particularly suitable for reducing the exposure of health-care operatives to radiation energy. In this case, both the container and the lid will be made of transparent material, either polymethyl methacrylate or glass, rich in lead or tungsten depending on the gamma emission energy. In this case, the second infusion catheter, too, that conveys the radiopharmaceutical to the patient will be housed in appropriately shielded guides.

In this particular case, the container and lid will be made of polymethyl methacrylate containing a certain amount of lead such as to ensure the necessary radiation protection and transparency of the receptacle and lid walls. In this realisation, too, the choice of material and determination of the thicknesses of the receptacle and lid walls are matters which come within the field of expertise of the average technician in the sector.

The container according to the present invention affords the advantage of allowing the shipment or transportation of precalibrated and customised radiopharmaceuticals for individual patients. Inside the container the operator can check the volume/quantity desired without having to handle the vial.

The above-described container allows infusion of the radiopharmaceutical in a patient or its transfer elsewhere without needing to manipulate the vial. The operator, in fact, can extract the radiopharmaceutical with a syringe while the vial containing it remains housed in the container, which affords effective radioprotection.

The invention, however, solves the problem posed of allowing infusion in a patient or transfer elsewhere to another radiopharmaceutical receptacle, without needing to aspirate it from its vial with a syringe, and of accurately checking the volume of radiopharmaceutical infused in the patient or transferred to another receptacle.

For this purpose, the invention provides a set for infusion of a radiopharmaceutical in a patient or for its transfer elsewhere from its vial housed in the container. The infusion set described above, combined with the container housing the vial of radiopharmaceutical, constitutes a complete kit for managing the radiopharmaceutical without any manipulation and without the operator having to perform a direct extraction operation.

Reference is made to FIGS. 3 and 4, that show part of the set and container 1-2 and the set according to the invention in an infusion operation, respectively.

The set contains, in combination with container 1-2 of a vial of radiopharmaceutical 3, a conventional bottle 4 containing saline, an infusion catheter and a second infusion catheter, marked collectively 5 and 6, respectively.

The saline bottle 4 may be, for example, 250 ml. Details regarding the use of the saline solution will be provided here below.

The first infusion catheter 5 is conventionally equipped with twin connectors, with a first needle 50, a flow regulator 51 and a second needle 52. Needle 50 is of known type, suitable for insertion in the bottle of saline solution 4 and is connected to a drop-counter 53. The drop-counter is connected via a small tube 54, and connector 55, to the second needle 52, which is a metal infusion needle.

The second infusion catheter 6, according to the invention described herein, is equipped with twin connectors, with a first needle 60, a flow regulator 61 and a second needle 62. Needle 60 is of the infusion type and is connected via connector 63 and small tube 64 to the second needle 62, which is also an infusion needle, via connector 65.

In an infusion operation illustrated in FIG. 4, saline bottle 4 is conventionally suspended in a cradle 7 attached to a stand 8, equipped with a support shelf 9. The first infusion catheter is inserted with the first needle 50 in the cap of bottle 4, while the second needle 52 is inserted, via flared portion 27 and central through-hole 26 of lid 2, into the cap of radiopharmaceutical vial 3 in such a way as not to be immersed in the pharmaceutical. As shown in FIG. 5, which is an enlarged view of a detail of FIG. 4, the initial level of radiopharmaceutical is marked L.

The second infusion catheter 6 also has its first needle 60 inserted via flared portion 27 and through-hole 26 of lid 2, into the cap of the vial of radiopharmaceutical, whereas the second needle 62 is inserted in the brachial vein B of a patient. The first needle 60 is long enough to touch the bottom of the vial of radiopharmaceutical, where it must be held in place for the complete extraction of the radiopharmaceutical, as shown in FIG. 5.

The provision of flow via the bottle of saline solution 4, the first infusion catheter 5, vial 3 in container 1-2, and the second infusion catheter 6 allows the radiopharmaceutical to be delivered by gravity. The saline solution is fed from bottle 4 into radiopharmaceutical vial 3 with flow regulation by means of flow-regulator 51. The influx of saline brings about an increase in pressure in radiopharmaceutical vial 3 which has its entire contents aspirated by the second infusion catheter 6, the flow rate of which is regulated by flow-regulator 61.

If one desires to transfer the radiopharmaceutical elsewhere, the transfer is accomplished using air or some other suitable gaseous liquid as the vector fluid. For this purpose, either the infusion catheter which is part of the present invention or any other suitable means can be used.

The same kit described above can be used for the transfer of the radiopharmaceutical from its vial to another receptacle, for example in order to fractionate the doses, using air as the driving medium.

Disposal of the kit is also risk-free for the operator. The infusion catheters, and particularly the second infusion catheter, are destined to be treated as hazardous materials, as is the radiopharmaceutical vial. After extracting the catheters and unscrewing the lid, the radiopharmaceutical vial is dropped out of its container into the radioactive waste collector, while the container according to the invention can be reused.

In addition, the container according to the invention is suitable for use with automatic and even robotic systems for the preparation of individual doses.

The container according to the invention and its infusion set are also suitable for managing generally toxic drugs, such as, for example, anticancer agents.

The invention claimed is:

1. Container for a radiopharmaceutical vial containing a radiopharmaceutical to be extracted via a needle inserted into a sealed cap secured to the mouth of the radiopharmaceutical vial, said container being made of a material suitable for shielding the operator from radiations emitted by the radiopharmaceutical through the vial, and consisting of a receptacle, made of transparent material, with a cavity capable of containing the vial of radiopharmaceutical, and of a lid coupled to the receptacle for closing the container, wherein said lid presents a central through-hole, said central through-hole being provided above an upper compartment for housing the mouth of the vial, said upper compartment being provided in the lid and flaring downward into a hollow truncated-cone portion.

2. Container according to claim 1, wherein said through-hole presents an outward facing upper flared portion.

3. Container according to claim 1, wherein the vial of radiopharmaceutical is mobilely coupled to the cavity of the receptacle, wherein, when the container is in the closed position, the lid is in contact with the mouth of the vial of radiopharmaceutical, the central through-hole in the lid being situated above the cap of the vial of radiopharmaceutical.

4. Container according to claim 1, wherein the radiations emitted by the radiopharmaceutical are beta-radiations and the material of which the receptacle and the lid are made is polymethyl methacrylate.

5. Container according to claim 1, wherein the radiations emitted by the radiopharmaceutical are beta and gamma radiations and the material of which the receptacle and lid are made is polymethyl methacrylate containing lead as an additive.

6. Container according to claim 1, wherein the radiopharmaceutical contains [$^{18}$F]FDG.

7. Container according to claim 1, wherein the lid is made of transparent material.

8. Container according to claim 1, wherein the receptacle has a cylindrical outer surface.

9. Container according to claim 1, wherein the receptacle includes a generally cylindrical inner surface having a height dimensioned to be less than the height of the vial, such that the vial projects above the generally cylindrical inner surface in use.

10. Container according to claim 1, wherein transparent material of said receptacle is positioned so as to enable viewing of the entire outer circumferential surface of the vial.

11. Container for a radiopharmaceutical vial containing a radiopharmaceutical to be extracted via a needle inserted into a sealed cap secured to the mouth of the radiopharmaceutical vial, said container being made of a material suitable for shielding the operator from radiations emitted by the radiopharmaceutical through the vial, and consisting of a receptacle, made of transparent material, with a cavity capable of containing the vial of radiopharmaceutical, and of a lid coupled to the receptacle for closing the container, wherein said lid presents a central through-hole, said central through-hole being provided above an upper compartment for housing the mouth of the vial, wherein said upper compartment flares downward into a hollow truncated-cone portion.

12. Container according to claim 11, wherein said through-hole presents an outward facing upper flared portion.

13. Container according to claim 11, wherein the vial of radiopharmaceutical is mobilely coupled to the cavity of the receptacle, wherein, when the container is in the closed position, the lid is in contact with the mouth of the vial of radiopharmaceutical, the central through-hole in the lid being situated above the cap of the vial of radiopharmaceutical.

14. Container according to claim 11, wherein radiations emitted by the radiopharmaceutical are beta-radiations and the material of which the receptacle and the lid are made is polymethyl methacrylate.

15. Container according to claim 11, wherein radiations emitted by the radiopharmaceutical are beta and gamma radiations and the material of which the receptacle and lid are made is polymethyl methacrylate containing lead as an additive.

16. Container according to claim 11, wherein the radiopharmaceutical contains [hu 18F]FDG.

17. Container according to claim 11, wherein the receptacle has a cylindrical outer surface.

18. Container according to claim 11, wherein the receptacle includes a generally cylindrical inner surface having a height dimensioned to be less than the height of the vial, such that the vial projects above the generally cylindrical inner surface in use.

19. Container according to claim 11, wherein transparent material of said receptacle is positioned so as to enable viewing of the entire outer circumferential surface of the vial.

20. Container for radiopharmaceutical vial containing a radiopharmaceutical to be extracted via a needle inserted into a sealed cap secured to the mouth of the radiopharmaceutical vial, said container being made of a material suitable for shielding the operator from radiations emitted by the radiopharmaceutical through the vial, and consisting of a receptacle, made of transparent material, with a cavity capable of containing the vial of radiopharmaceutical, and of a lid coupled to the receptacle for closing the container, wherein said lid presents a central through-hole, said central through-hole being provided above an upper compartment for housing the mouth of the vial, said upper compartment being provided in the lid, wherein the radiations emitted by the radiopharmaceutical are beta and gamma radiations and the material of which the receptacle and lid are made is polymethyl methacrylate containing lead as an additive.

21. Container according to claim 20, wherein said upper compartment flares downwards into a hollow truncated-cone portion.

22. Container according to claim 20, wherein said through-hole presents an outward facing upper flared portion.

23. Container according to claim 20, wherein the vial of radiopharmaceutical is mobilely coupled to the cavity of the receptacle, wherein, when the container is in the closed position, the lid is in contact with the mouth of the vial of radiopharmaceutical, the central through-hole in the lid being situated above the cap of the vial of radiopharmaceutical.

24. Container according to claim 20, wherein the radiations emitted by the radiopharmaceutical are beta-radiations and the material of which the receptacle and the lid are made is polymethyl methacrylate.

25. Container according to claim 20, wherein the radiopharmaceutical contains [18]FDG.

26. Container according to claim 20, wherein the lid is made of transparent material.

27. Container according to claim 20, wherein the receptacle has a cylindrical outer surface.

28. Container according to claim 20, wherein the receptacle includes a generally cylindrical inner surface having a height dimensioned to be less than the height of the vial, such that the vial projects above the generally cylindrical inner surface in use.

29. Container according to claim 20, wherein transparent material of said receptacle is positioned so as to enable viewing of the entire outer circumferential surface of the vial.

* * * * *